US012797525B2

(12) United States Patent
Omlor et al.

(10) Patent No.: US 12,797,525 B2
(45) Date of Patent: Nov. 17, 2026

(54) DEVICE FOR REMOVING A GAS FROM AN AQUEOUS LIQUID

(71) Applicant: UNIVERSITAET DES SAARLANDES, Saarbruecken (DE)

(72) Inventors: Albert Omlor, Homburg (DE); Philipp Lepper, Homburg (DE)

(73) Assignee: UNIVERSITAET DES SAARLANDES, Saarbruecken (DE)

( * ) Notice: Subject to any disclaimer, the term of this patent is extended or adjusted under 35 U.S.C. 154(b) by 948 days.

(21) Appl. No.: 17/800,483

(22) PCT Filed: Feb. 17, 2021

(86) PCT No.: PCT/EP2021/053800
§ 371 (c)(1),
(2) Date: Aug. 17, 2022

(87) PCT Pub. No.: WO2021/165277
PCT Pub. Date: Aug. 26, 2021

(65) Prior Publication Data

US 2023/0083534 A1 Mar. 16, 2023

(30) Foreign Application Priority Data

Feb. 18, 2020 (DE) ..................... 10 2020 104 117.9

(51) Int. Cl.
*A61M 1/16* (2006.01)
*A61M 1/36* (2006.01)
(Continued)

(52) U.S. Cl.
CPC ........ *A61M 1/1698* (2013.01); *A61M 1/3687* (2013.01); *B01D 19/0005* (2013.01);
(Continued)

(58) Field of Classification Search
CPC ...... B01D 61/32; B01D 61/28; B01D 61/243; B01D 63/031; B01D 63/02;
(Continued)

(56) References Cited

U.S. PATENT DOCUMENTS

2019/0030232 A1 1/2019 Kreymann et al.

FOREIGN PATENT DOCUMENTS

DE 102009008601 A1 8/2010
IT BO20090437 A1 1/2011
(Continued)

OTHER PUBLICATIONS

JP Patent Application No. 2022-549418, filed Feb. 17, 2021; Notice of Reasons for Rejection issued Nov. 14, 2024; 8 pages [with English translation].

*Primary Examiner* — Allison G Fitzsimmons
(74) *Attorney, Agent, or Firm* — Mueting Raasch Group

(57) ABSTRACT

The invention relates to a device for removing a gas from an aqueous liquid, particularly a blood liquid, comprising a first compartment permeated by the aqueous liquid during operation of the device; a second compartment permeated by a purging gas during operation of the device, the first compartment and the second compartment being separated from each other by a semipermeable membrane; and a third compartment permeated by a liquid proton donor during operation of device, said proton donor being an organic or inorganic acid, the first compartment and the third compartment being separated from each other by a membrane permeable to ions, and the membrane permeable to ions comprising at least one cation conductor.

20 Claims, 2 Drawing Sheets

(51) Int. Cl.
*B01D 19/00* (2006.01)
*B01D 63/02* (2006.01)
*B01D 63/04* (2006.01)
*B01D 71/26* (2006.01)

(52) U.S. Cl.
CPC ....... *B01D 19/0031* (2013.01); *B01D 63/034* (2022.08); *B01D 63/04* (2013.01); *B01D 71/26* (2013.01)

(58) Field of Classification Search
CPC ............ B01D 2311/14; B01D 2311/13; B01D 2311/16; B01D 2313/21; B01D 2313/44; A61M 1/1601; A61M 1/1613; A61M 1/1698; A61M 1/3403; A61M 1/1605; A61M 1/16; A61M 1/1617; A61M 1/3413; A61M 1/34; A61M 1/342; A61M 1/3434; A61M 1/3437; A61M 1/3635; A61M 1/1654; A61M 2205/3334; A61M 2230/208
See application file for complete search history.

(56) References Cited

FOREIGN PATENT DOCUMENTS

| | | | |
|---|---|---|---|
| JP | 7785357 | B2 | 12/2025 |
| WO | 01/77284 | A2 | 10/2001 |
| WO | 2008/135282 | A2 | 11/2008 |
| WO | 2018/191364 | A1 | 10/2018 |
| WO | 2019/055933 | A2 | 3/2019 |

DEVICE FOR REMOVING A GAS FROM AN AQUEOUS LIQUID

PRIORITY CLAIM

This application claims priority to International Application No. PCT/EP2021/053800, filed Feb. 17, 2021, which claims priority to German Application No. 10 2020 104 117.9, filed Feb. 18, 2020, wherein the contents of said applications are incorporated herein by reference in their entireties.

The invention relates to a device for removing a gas from an aqueous liquid, preferably a blood liquid. The invention further relates to a composition comprising a liquid proton donor and a use of the composition for treating hypercapnia.

Hypercapnia refers to an increased level of carbon dioxide in the blood. The presence of carbon dioxide in the blood is normal, as a waste product of cellular metabolism. The carbon dioxide is transported out of the cells into the lungs by means of blood circulation and is exhaled there. When the lung is insufficiently ventilated, for example in the case of a lung disease or lung failure, then carbon dioxide accumulates in the blood. This results in respiratory acidosis of the blood, potentially leading to death if the pH value drops below 7.0.

In such a situation, the carbon dioxide must be removed from the blood as quickly as possible. Because the affected patient cannot accomplish this on his own, extracorporeal membrane oxygenation (ECMO) is typically used, wherein the blood interacts with a purging gas (sweeping gas) across a membrane. Carbon dioxide is removed from the blood across the membrane in the oxygenator and simultaneously has oxygen added. For membrane oxygenation, large vessels (e.g., vena femoralis or vena jugularis interna) are used for removing and returning the blood. Therefore a not insignificant amount of blood removed from the patient circulates in the ECMO machine while the method is performed.

The object of the present invention is to improve the removing of carbon dioxide from an aqueous liquid, particularly in the case of a blood liquid such that the removing of carbon dioxide can be performed by means of a relatively small access to the patient and is simultaneously more efficient, so that less blood can be taken from the patient and the procedure can remove a sufficient proportion of the carbon dioxide present in the blood in a short(er) time.

According to the invention, a device for removing a gas from an aqueous liquid is provided, comprising: a first compartment permeated by the aqueous liquid during operation the device, a second compartment permeated by a purging gas during operation the device, the first compartment and the second compartment being separated from each other by a semipermeable membrane, and a third compartment permeated by a liquid proton donor during operation the device, the first compartment and the third compartment being separated from each other by a membrane permeable to ions.

The device according to the invention serves for at least partially removing a gas from an aqueous liquid, particularly for at least partially removing carbon dioxide from blood. Each of the compartments is part of an individual circulation and is permeated by a corresponding substance during operation. A pump can be provided in each of the circulations and serve for implementing a corresponding flow. The device according to the invention is implemented such that the substance in the first compartment interacts during operation with the substance in the second compartment through the semipermeable membrane and the substance in the first compartment simultaneously interacts during operation with the substance in the third compartment through the membrane permeable to ions. The substances flowing through the second and third compartments, in contrast, do not interact with each other. Said feature is achieved in that the second compartment and the third compartment are spatially separated from each other such that the substance in the second compartment does not directly contact the membrane permeable to ions of the third compartment, and conversely the substance in the third compartment does not directly contact the semipermeable membrane of the second compartment. Interacting means here a material exchange between two substances through a separating layer, such as a membrane. Due to suitable interacting of the substance in the first compartment with the substance in the second compartment and with the substance in the third compartment, the gas is at least partially removed from the substance in the first compartment, that is, from the aqueous liquid. The suitable or desired interacting can be achieved by providing concentration gradients between the first and second compartment and between the first and third compartment with respect to a gas to be removed and to the relevant ions. The liquid proton donor can be an organic or inorganic acid, such as hydrochloric acid (HCl). The liquid proton donor is preferably non-toxic. A buffer solution can also be used, comprising an equal amount of ions (e.g., hydrogen cations) but having a more moderate pH value in comparison with hydrochloric acid (such as 6.9).

According to further embodiments of the device, the aqueous liquid can be a blood liquid, preferably blood. Carbon dioxide can then particularly be at least partially removed from blood by means of the device. In this context, the purging gas can be pure oxygen, as is typical for ECMO applications. In the case of blood as the aqueous liquid, the device can be seen as an expanded ECMO machine, wherein the third compartment, permeated with the liquid proton donor, is additionally provided in the membrane oxygenator in which carbon dioxide is removed from the blood and has oxygen added thereto.

Due to the interaction between the blood liquid and the purging gas through the semipermeable membrane, the carbon dioxide physically dissolved in the blood transfers into the purging gas and is thus removed from the blood liquid. The physically dissolved (physically bonded) carbon dioxide is understood to be carbon dioxide dissolved as a gas in the blood liquid. At the same time, the blood is enriched with oxygen from the purging gas. Said process corresponds to the conventional oxygenation of the blood through an ECMO or ECCO2R membrane (ECCO2R: extracorporeal $CO_2$ removal). Due to the interaction between the blood liquid and the liquid proton donor through the membrane permeable to ions, chemically dissolved carbon dioxide in the blood liquid reacts with hydrogen ions (H+) diffusing through the membrane out of the liquid proton donor into the blood liquid. Chemically dissolved (chemically bonded) carbon dioxide is understood to be carbon dioxide "captured" in bicarbonate compounds, such as potassium hydrogen carbonate, sodium hydrogen carbonate, or magnesium bicarbonate. A proton exchange thereby takes place between the liquid proton donor, such as hydrochloric acid (HCl), and the bicarbonate compound present in the blood liquid, thereby forming carbonic acid ($H_2CO_3$). Said acid, however, is very unstable and decomposes into water ($H_2O$) and carbon dioxide ($CO_2$). Said carbon dioxide is now released from the original bicarbonate compound thereof and is available for transporting away by means of the purging gas. The proton exchange, wherein a cation transitions out of the blood liquid on the side of the liquid proton donor in exchange for the hydrogen cation (H+) provided thereby, ensures that no electrical potential arises between the substances within the device according to the invention and thus the substances and the device remain electrically neutral.

The liquid proton donor can comprise potassium and/or calcium and/or magnesium, for example, so that a concentration gradient toward the blood liquid with respect to said materials, by means of which said physiologically important minerals would be removed from the blood, can be avoided. In other words, an equilibrium of electrochemical potential with respect to particular materials (such as potassium and calcium) is sought between the liquid proton donor and the blood liquid, so that said materials are not removed from the blood liquid and do not transition to the liquid proton donor. Sodium can be preferably removed from the blood liquid during the induced ion exchange and can transition into the liquid proton donor through the membrane permeable to ions as an exchange cation. The diffusion of sodium as an exchange ion can be adjusted by means of a corresponding concentration gradient between the blood liquid and the liquid proton donor with respect to said material. For this purpose in particular, the liquid proton donor can contain no sodium.

By providing the third compartment permeated by the liquid proton donor, an additional mechanism is thus provided by means of which additional carbon dioxide can be removed from the blood in comparison with the typical ECMO treatment. In other words, an additional source of carbon dioxide in the blood liquid can be “tapped”, whereby carbon dioxide is more efficiently and quickly eliminated. It is thereby possible to operate the device according to the invention using a smaller amount of blood than for a typical ECMO treatment, so that a smaller access point is sufficient and a large blood vessel does not need to be used for removing blood. The device according to the invention can thus provide sufficient removing of carbon dioxide from the blood liquid at a blood access point at which about 400 ml of blood is taken per minute. It is further advantageous that using the device according to the invention can set respiration more protectively, e.g., at lower respiration pressures, thereby causing less damage to the lungs.

The device according to the invention can be implemented such that the second and third compartments each comprise a plurality of elongated structures, for example a plurality of hollow channels, for example in the form of hollow fibers. A long compartment length (and a correspondingly adjusted permeating speed) can cause the enriching of blood liquid with protons of the liquid proton donor to take place slowly, so that a pH shock can be avoided. The time of contact between the substances in the first and third compartments is determinative here.

According to further embodiments of the device, the second compartment can be bounded by or comprise a plurality of lines, preferably hollow fibers, made of the semipermeable material. The lines can be made substantially of polyolefin, for example, and can comprise polymethylpentene (PMP), for example. The lines forming the second compartment can all have a common inlet and outlet separate from the inlets and outlets of the other compartments.

According to further embodiments of the device, the third compartment can be bounded by or comprise a plurality of lines, preferably hollow fibers, made of the material permeable to ions. The lines can be made of a plastic permeable to ions, particularly to hydrogen cations. The lines forming the third compartment can all have a common inlet and outlet separate from the inlets and outlets of the other compartments.

According to further embodiments of the device, the membrane permeable to ions can comprise a cation conductor, such as Nafion, or a cation and anion conductor. The cation conductor can be selective. For the case of a non-selective cation conductor, the selectivity with respect to the permeability thereof can be achieved in that a concentration gradient between the aqueous liquid and the liquid proton donor is produced for the cations participating in the ion exchange (such as $H^+$ and $Na^+$). For those cations not intended to participate in the ion exchange (such as the physiologically relevant $K^+$, $Ca^{2+}$, $Mg^{2+}$ in the case of blood), in contrast, diffusing from the blood liquid into the liquid proton donor is prevented in that at least the same concentration of said ions is present in the proton donor as in the blood liquid. The membrane permeable to ions can also be a plastic permeable to both anions and cations, that is, an ion conductor.

The membrane permeable to ions is understood to be a membrane permeable only to ions but not, in contrast, to neutral atoms and molecules. The membrane permeable to ions can further be permeable only for particular ions, for example ions up to a particular ion radius. An ion exchanger membrane can also be meant by the membrane permeable to ions, that is, an ion exchanger processed into a thin film. The ion exchanger membrane can be used for allowing selectively determined ions to pass through. The ion exchanger membrane can thus be permeable only for cations (a cation conductor) or for both cations and anions (a cation and anion conductor).

One preferred cation conductor is Nafion. Nafion (2-[1-[difluoro-[(trifluoroethenyl)oxy]methyl]-1,2,2,2-tetrafluoroethoxy]-1,1,2,2-tetrafluoroethane sulfonic acid; CAS-Number: 31175-20-9) is a perforated copolymer comprising a sulfonic group as the ionic group. The substructures of Nafion are perfluoro-3,6-dioxa-4-methyl-7-octene-1-sulfonic acid and tetrafluoroethene. The acidic sulfonic acid groups in Nafion enable a perfluoridated polymer having ionic properties. Nafion is selectively conductive for protons and other cations. Nafion thus has a blocking effect for anions.

The electrical exchange for shifting cations of the liquid proton donor (e.g., $H^+$) could then take place in addition to shifting target cations out of the blood liquid, such as $Na^+$, also by shifting anions out of the liquid proton donor, such as in the case of hydrochloric acid as a liquid proton donor. At the same time, however, care should thereby also be taken to avoid undesired shifting of anions out of the blood liquid into the liquid proton donor in return.

According to further embodiments of the device, the lines of the second compartment and the lines of the third compartment can be present in the first compartment, except for the inlets and outlets thereof. The surface area available for the interaction between the substances of the first and second compartment and between the substances of the first and third compartment can thereby be maximized. By separating the inlets and outlets of the compartments, the flow rate and the flow direction for the corresponding substance can be set individually in each.

According to further embodiments of the device, the lines of the second compartment and the lines of the third compartment can always be separated from each other by a partial volume of the first compartment. In other words, the lines of the second compartment and the lines of the third compartment are disposed spaced apart from each other, so that the substance present in the first compartment can flow in between said lines. Said design is advantageous because the substance in the first compartment is the target substance for the interaction with the substances in the second and third compartment.

According to further embodiments of the device, the first compartment can comprise an inlet and an outlet in order to guide blood through the first compartment, wherein the inlet and the outlet are disposed such that a flow of the aqueous liquid through the first compartment can be adjusted during operation of the device. The inlet and outlet can advantageously be disposed on opposite sides of the compartment, so that the aqueous liquid substantially flows through the entire first compartment (vertically, horizontally, or diagonally with respect to the direction of gravity) in order to reach the outlet thereof from the inlet thereof.

The device according to the invention can comprise additional fluidic elements such as flow limiters, heaters, and the like. A pH sensor, for example, can be present in the circulation circulating through the third compartment, for example. A closed-loop control circuit can thereby be provided, wherein the pH value of the liquid proton donor can be automatically regulated to the pH value of the blood. If the pH value of the liquid proton donor is too low, for example, the flow speed thereof through the third compartment can be slowed down. Alternatively, the pH sensor can also be provided in the first compartment in order to directly measure the pH value of the aqueous liquid.

In various embodiments, a composition is further provided, comprising a liquid proton donor permeating the third compartment of the device according to the invention for use in a method for treating or therapy of hypercapnia.

In various embodiments, a use of a composition comprising a liquid proton donor is provided for permeating the third compartment of the device according to the invention for treating hypercapnia. The use of the composition can also comprise the first compartment of the device according to the invention being permeated by blood and the second compartment of the device according to the invention being permeated by a purging gas.

According to further embodiments of the composition or of the use according to the invention of the composition, the liquid proton donor can comprise a preferably non-toxic acid, such as hydrochloric acid, or an acidic buffer solution. The acidic buffer solution can be slightly more acidic relative to the physiological pH value of blood, said value being between 7.35 and 7.45 for humans, and can have, for example, a pH value in the range between 6.5 and 7. In further embodiment examples, the acidic buffer solution can have a pH value in the range between 4 and 6.5, preferably between 4 and 6, further preferably between 4 and 5.5, further preferably between 4 and 5, further preferably between 4 and 4.5.

According to further embodiments of the composition or of the use according to the invention of the composition, at least one physiologically relevant type of metal cation can be present in at least a physiological concentration in the liquid proton donor. A plurality or substantially all of the physiologically relevant metal cations ($K^+$, $Ca^{2+}$, and $Mg^{2+}$) can preferably be present in at least the corresponding physiological concentration thereof in the liquid proton donor. In other words, the physiologically relevant metal cations can be present in the liquid proton donor at the same or higher concentration as in blood plasma in each case. It can thereby be prevented that the physiologically relevant metal cations are removed from the blood and diffuse into the third compartment due to a concentration gradient. There is, however, preferably no sodium present in the liquid proton donor. A concentration gradient thereby arises during operation of the device according to the invention between the first compartment and the third compartment with respect to sodium, whereby, as previously explained, a selection is made with respect to the exchange cation diffusing into the third compartment out of the first compartment in return for the hydrogen cation donated by the liquid proton donor.

According to further embodiments of the composition according to the invention or the use according to the invention of the composition, the hypercapnia can be caused by COPD (chronic obstructive pulmonary disease), ARDS (acute respiratory distress syndrome), asthma, pneumonia, or sleep apnea.

According to further embodiments of the composition or of the use according to the invention of the composition, the composition can further comprise a purging gas permeating the second compartment of a device described herein. The purging gas can be the purging gas typically used for an ECMO treatment.

According to further embodiments of the composition or of the use according to the invention of the composition, the treatment can comprise the following steps: providing a flow of the aqueous liquid through the first compartment; providing a flow of the purging gas through the second compartment; and providing a flow of the liquid proton donor through the third compartment.

Preferred embodiment examples of the invention are described in more detail below using the attached drawings.

Figure 1:
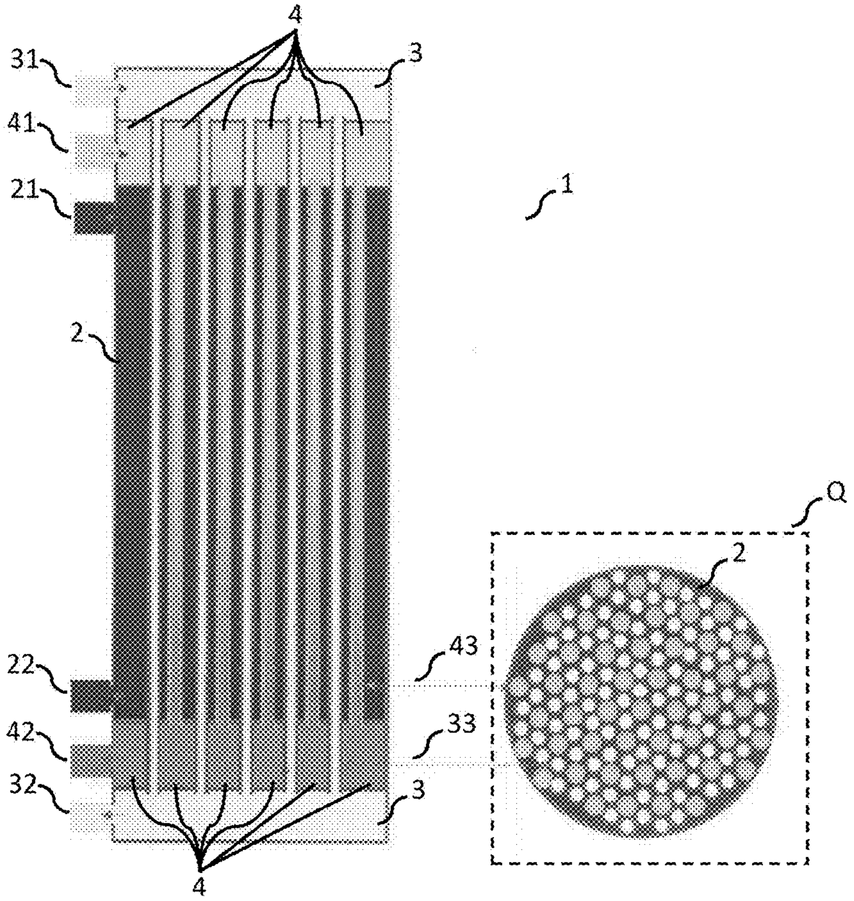
FIG. 1 shows the schematic structure of a device for removing a gas from an aqueous liquid according to various embodiment examples.

FIG. 1 shows a side view of a schematic structure of the device 1 according to the invention for removing a gas from an aqueous liquid. The depiction focuses on the interaction space of the device 1, that is, the region in which the substances in the corresponding compartments can interact with each other; the other fluidic components (lines, pumps, sensors, etc.) are not depicted. The device 1 comprises a first compartment 2, a second compartment 3, and a third compartment 4. Each of the compartments 2, 3, 4 comprises two connections: the first compartment 2 comprises a first connection 21 and a second connection 22, the second compartment 3 comprises a third connection 31 and a fourth connection 32, and the third compartment 4 comprises a fifth connection 41 and a sixth connection 42. One connection of each of the compartments 2, 3, 4 functions as an inlet during operation of the device according to the invention and the corresponding other connection functions as an outlet, depending on the direction in which the corresponding substance permeates the corresponding compartment. A pump, for example, can be disposed between each pair of connections of a compartment 2, 3, 4 in order to maintain circulation of the substance.

The first compartment 2 permeated by the aqueous liquid can comprise any arbitrary shape, for example a cylindrical shape as shown in FIG. 1. One connection each can be disposed near the floor and near the cover of a compartment. The second compartment 3 comprises a plurality of first lines 33, preferably hollow fibers, providing a fluid connection between the third connection 31 and the fourth connection 32. The third connection 31 and the fourth connection 32 each open into a reservoir in the top and in the bottom region of the interaction space of the device 1, wherein said reservoir is not a necessary feature, wherein each reservoir in the embodiment example shown extends over the entire base surface of the interaction space. The first lines 33 connect the two reservoirs to each other. In an analogous manner, the third compartment 4 comprises a plurality of second lines 43, preferably hollow fibers, disposed between the fifth connection 41 and the sixth connection 42. The fifth connection 41 and the sixth connection 42 each open into a reservoir in the top and in the bottom region of the interaction space of the device 1, wherein each reservoir in the embodiment example shown extends over the entire base surface of the interaction space 1. Because the reservoirs of the second compartment 3 enclose the reservoirs of the third compartment 4 or are disposed above and below the same as viewed from outside, the first lines 33 run through the reservoirs of the third compartment 4. To this end, the second lines 43 of the third compartment 4 are advantageously longer in design than the first lines 33 of the second compartment 3, because the first lines also run through the reservoirs of the third compartment 4. A plan view of a cross section Q in the center region of the interaction space is shown on the right side of the side view of the interaction space of the device 1. The cross section view Q shows that the first lines 33 of the second compartment 3 and the second lines 43 of the third compartment 4 each run through the first compartment 2 spaced apart from each other by a distance. The first lines 33 and the second lines 43 are also disposed spaced apart from each other by a distance in the volume of the first compartment 2.

It is noted that the arrangement and location of the second compartment 3 and of the third compartment 4, as shown in FIG. 1, embodies one of many potential arrangements. In a further embodiment example, the location of the second and third compartments 3, 4, as shown in FIG. 1, can be swapped with each other. Furthermore, the flow direction (from top to bottom or from bottom to top in FIG. 1) of the substance flowing in each of compartments 2, 3, 4 can generally be adjusted individually and independently of the other two compartments in each case. The quantity and the cross section of the first lines 33 and the second lines 43 can be selected as needed.

Figure 2:
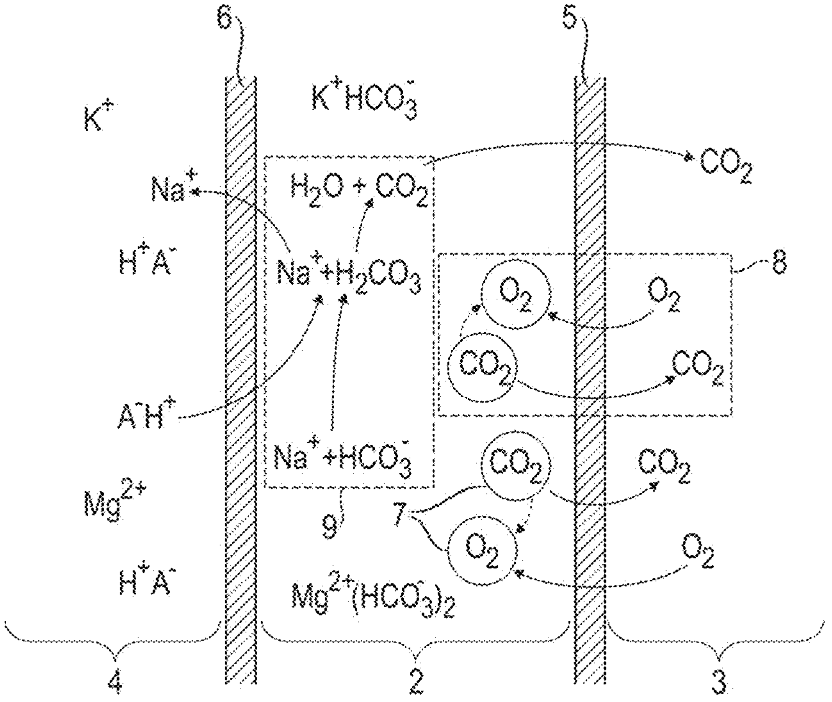
FIG. 2 shows a schematic view of the three compartments and the chemical reactions occurring during operation of the device according to the invention.

FIG. 2 shows the chemical processes occurring during operation of the device 1 according to the invention between the first and second compartment 2, 3 and between the first and third compartment 2, 4. The first compartment 2 is permeated by the aqueous liquid, preferably blood, from which a gas, preferably carbon dioxide, is to be removed. Physically dissolved carbon dioxide is present in the blood liquid. In addition, physiologically relevant metal cations are present in the blood liquid at the corresponding physiological concentration of each. Said metal cations are bound in bicarbonate compounds. At the same time, carbon dioxide is chemically bound in the bicarbonate compounds.

The purging gas, typically comprising pure oxygen ($O_2$) flows through the second compartment 3. The semipermeable membrane 5 is disposed between the first compartment 2 and the third compartment 3. Due to a concentration gradient between the first compartment 2 and the second compartment 3 with respect to carbon dioxide ($CO_2$), the carbon dioxide physically bound in the blood 7 is released and diffuses across the semipermeable membrane 5 into the second compartment 3. In return, oxygen diffuses out of the purging gas, across the semipermeable membrane 5, into the blood liquid, and is received by the erythrocytes 7 therein. Said procedure is well known from typical ECMO applications and is sketched in the first marked region 8.

The carbon dioxide chemically bonded in the bicarbonate compounds is released from the bicarbonate compounds by means of the liquid proton donor permeating the third compartment 4. A cation exchange occurs through the membrane 6 permeable to ions disposed between the first compartment 2 and the third compartment 4, and said exchange is further sketched in the second marked region 9. Said procedure is also induced by a concentration gradient with respect to an exchange ion. In the embodiment example shown for oxygenation of blood, the exchange ion is sodium ($Na^+$), the target exchange ion in the example shown. The sodium diffuses through the membrane 6 permeable to ions into the (low-sodium) third compartment 4. In return, hydrogen cations present in the liquid proton donor diffuse out of the third compartment 4 into the first compartment 2. The hydrogen cation bonds to the bicarbonate ($HCO^-_3$), whereby carbonic acid ($H_2CO_3$) is formed, but is unstable and ultimately relatively quickly decomposes into water ($H_2O$) and carbon dioxide. The carbon dioxide molecule thus released crosses the semipermeable membrane 5 into the second compartment 3 in a manner analogous to the physically dissolved carbon dioxide molecules. The liquid proton donor in the third compartment 4 thereby serves for releasing the chemically bonded carbon dioxide, while the removing of the carbon dioxide thus released out of the blood liquid takes place, as previously, by means of the purging gas permeating the second compartment 3.

In general, there are many different possibilities for the design of the interaction space between the three substances, particularly for the spatial arrangement of the first lines 33 of the second compartment 3 and the second lines 43 of the third compartment 4 relative to each other and within the first compartment 2. Three fundamental embodiments are sketched in the FIGS. 3A through 3C. A bar in each of the figures represents a compartment in the interaction region of the device 1 and is correspondingly labeled with the reference numeral of the corresponding compartment. The longitudinal extent of each bar also defines the axis along which the corresponding compartment is permeated by the associated substance. Accordingly, two fundamental permeation flow directions arise for each compartment 2, 3, 4.

Figure 3A:
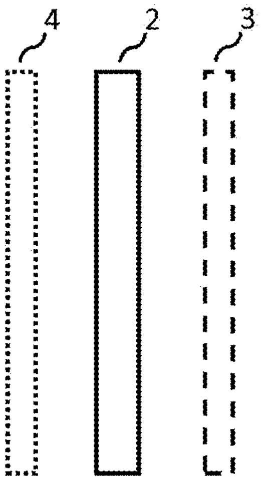
FIGS. 3A through 3C show potential locations of the three compartments of the device according to the invention relative to each other.

The embodiment sketched in FIG. 3A substantially corresponds to the embodiment of the device 1 according to the invention shown in FIG. 1, wherein the lines of the second compartment 3 and of the third compartment 4 are aligned parallel to each other and the flow directions of the substances through all three compartments 2, 3, 4 are aligned parallel to each other. The actual flow direction of the substance through each compartment can occur from top to bottom or from bottom to top, independently of the flow directions in the other two compartments. The location of the compartments 2, 3, 4 in the interaction region 1 sketched in FIG. 3A serves only for depicting the relative arrangement of the flow directions through the compartments relative to each other, so that the quantity of bars shown particularly does not correspond to the quantity of lines associated with a compartment. The quantity and the arrangement of the hollow channels forming the second compartment 3 and the third compartment 4 relative to each other can be implemented in various ways. One example of this is shown in the cross section view Q in FIG. 1, where it is evident that the first lines 33 form a hexagonal grid and the second lines 43 are disposed in the centers of the hexagons (except for the second lines 43 disposed on the edge). The lines of the second compartment 3 and of the third compartment 4 can further be disposed in alternating rows one after the other or adjacent to each other or in other geometric patterns.

Figure 3B:
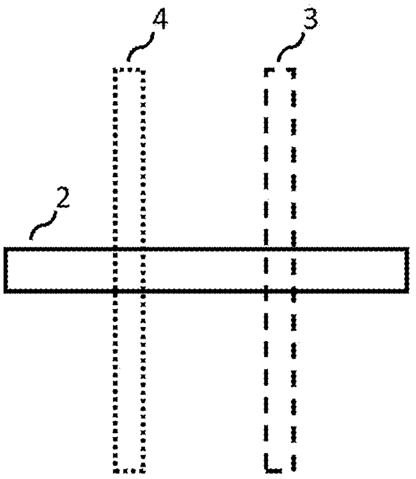

According to the arrangement of the compartments 2, 3, 4 relative to each other shown in FIG. 3B, the flow direction of the aqueous liquid through the first compartment 2 is perpendicular to the flow directions of the substances through the second compartment 3 and through the third compartment 4. The arrangement of the lines of the second compartment 3 and of the fourth compartment 4 relative to each other can fundamentally correspond to one of the arrangements mentioned with respect to FIG. 3A.

Figure 3C:
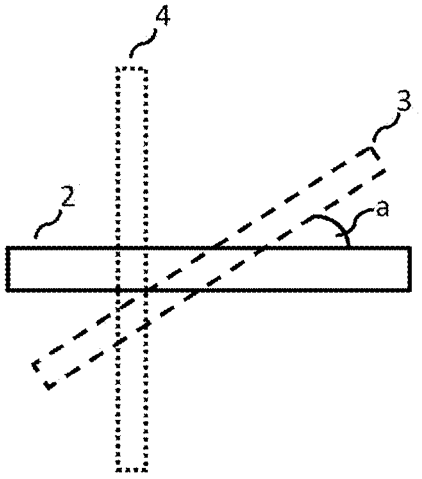

Finally, a further potential embodiment of the interaction space of the device is shown in FIG. 3C, wherein the flow direction through the second compartment 3 and through the third compartment 4 are perpendicular to the flow direction through the first compartment 2. In a modification of the embodiment shown in FIG. 3B, however, the hollow channels of the second compartment 3 are additionally disposed at an angle a to the hollow channels of the first compartment 2, so that the flow directions are also correspondingly disposed at the angle a relative to each other. The angle a can preferably be 90°, for example. The lines of the second compartment 3 and the second lines of the third compartment 4 can thereby substantially implement a rectangular or square grid structure (from the point of view of the aqueous liquid permeating the first compartment 2), the intermediate spaces thereof being permeated by the aqueous liquid. The grid structure can be implemented such that the lines of the second compartment 3 and the lines of the third compartment 4 contact each other and thus implement intersection points of the grid-like structure. Alternatively, the lines of the second component 3 and the lines of the third compartment 4 can be disposed perpendicular to each other in rows, the rows being spaced apart from each other.

The invention claimed is:

1. A device for removing a gas from an aqueous liquid, comprising:

a first compartment configured to be permeated by a blood liquid, optionally blood, during operation of the device;

a second compartment configured to be permeated by a purging gas during operation of the device, the first compartment and the second compartment being separated from each other by a semipermeable membrane; and a third compartment configured to be permeated by a liquid proton donor during operation of the device, said proton donor being an organic or inorganic acid, the first compartment and the third compartment being separated from each other by a membrane permeable to ions, the membrane permeable to ions comprising at least one cation conductor, wherein said membrane permeable to ions being an ion exchanger membrane permeable only for cations.

2. The device according to claim 1, the carbon dioxide dissolved in the blood liquid reacting with hydrogen ions of the proton donor and forming carbonic acid due to the interaction between the blood liquid and the liquid proton donor through the membrane permeable to ions, the hydrogen ions diffusing through the membrane permeable to ions out of the liquid proton donor into the blood liquid.

3. The device according to claim 1, the arising carbonic acid decomposing into water and carbon dioxide for transporting away by the purging gas of the second compartment.

4. The device according to claim 1, the second compartment comprising a plurality of lines, optionally hollow fibers, made of the semipermeable material.

5. The device according to claim 1, the third compartment comprising a plurality of lines, optionally hollow fibers, made of the membrane permeable to ions.

6. The device according to claim 1, the membrane permeable to ions comprising a cation and anion conductor.

7. The device according to claim 4, the lines of the second compartment and the lines of the third compartment being present in the first compartment, except for the inlets and outlets thereof.

8. The device according to claim 4, the lines of the second compartment and the lines of the third compartment always being separated from each other by a partial volume of the first compartment.

9. The device according to claim 4, the first compartment comprising an inlet and an outlet in order to guide the aqueous liquid through the first compartment, the inlet and the outlet being disposed such that a flow of blood through the first compartment can be adjusted during operation of the device.

10. A method for removing a gas from an aqueous liquid, comprising:

providing the aqueous liquid in the first compartment of the device according to claim 1;

providing a composition comprising a liquid proton donor and permeating the third compartment of the device therewith.

11. The method according to claim 10, the liquid proton donor being optionally a non-toxic acid or comprising an acidic buffer solution.

12. The method according to claim 10, at least one physiologically relevant type of metal cation being present in the liquid proton donor in at least a physiological concentration;

and no sodium being preferably present in the liquid proton donor.

13. The method according to claim 10, the composition further comprising a purging gas permeating the second compartment of the device according.

14. The method according to claim 10, the treatment comprising the following steps:

providing a flow of aqueous liquid through the first compartment;

providing a flow of the purging gas through the second compartment;

providing a flow of the liquid proton donor through the second compartment.

15. A method for treating hypercapnia comprising the step of using a composition comprising a liquid proton donor and permeating the third compartment of a device according to claim 1.

16. The method of claim 15, the liquid proton donor being an optionally non-toxic acid or comprising an acidic buffer solution.

17. The method of claim 15, at least one physiologically relevant type of metal cation being present in the liquid proton donor in at least a physiological concentration; and no sodium being optionally present in the liquid proton donor.

18. The method of claim 15, the composition further comprising a purging gas permeating the second compartment of the device according to claim 1.

19. The method of claim 15, the treatment comprising the following steps:

providing a flow of aqueous liquid through the first compartment;

providing a flow of the purging gas through the second compartment;

providing a flow of the liquid proton donor through the second compartment.

20. A device for removing a gas from an aqueous liquid, comprising:

a first compartment configured to be permeated by a blood liquid, optionally blood, during operation of the device;

a second compartment configured to be permeated by a purging gas during operation of the device, the first compartment and the second compartment being separated from each other by a semipermeable membrane; and a third compartment configured to be permeated by a liquid proton donor during operation of the device, said proton donor being an organic or inorganic acid, the first compartment and the third compartment being separated from each other by a membrane permeable to ions, the membrane permeable to ions comprising at least one cation conductor, wherein said membrane permeable to ions comprises a cation conductor comprising sulfonic acid groups.

* * * * *